United States Patent [19]

Katta et al.

[11] Patent Number: 5,378,833
[45] Date of Patent: Jan. 3, 1995

[54] METHOD FOR PREPARING GALACTO-OLIGOSACCHARIDES

[75] Inventors: Yasuo Katta, Kawanishi; Kazuhiro Ohkuma, Sanda; Mitsuko Satouchi, Takarazuka; Reiji Takahashi, Itami; Takehiko Yamamoto, Izumi, all of Japan

[73] Assignee: Matsutani Chemical Industries Co., Ltd., Hyogo, Japan

[21] Appl. No.: 633,834

[22] Filed: Dec. 26, 1990

[30] Foreign Application Priority Data

Dec. 26, 1989 [JP] Japan ................... 1-339133

[51] Int. Cl.$^6$ .................. C07G 17/00; C07H 1/00; C07H 5/04
[52] U.S. Cl. ..................... 536/124; 536/125; 536/123; 536/55.3; 536/1.11
[58] Field of Search ............ 536/124, 125, 18.6, 536/123, 55.3, 1.11; 514/54

[56] References Cited

U.S. PATENT DOCUMENTS

| | | | |
|---|---|---|---|
| 4,067,748 | 1/1978 | Rowe | 536/1.11 |
| 4,083,733 | 4/1978 | Asano et al. | 536/125 |
| 4,683,297 | 7/1987 | Yanami et al. | 536/18.6 |

FOREIGN PATENT DOCUMENTS 0272095 6/1988 European Pat. Off.

OTHER PUBLICATIONS

Patent Abstracts of Japan vol. 012, No. 186 (C-500) 31 May 1988 abstracting JP-A-62-292-791 (Samnatsu Kogyo KK) 19 Dec. 1987.

*Primary Examiner*—Jeffrey E. Russel
*Assistant Examiner*—Louise N. Leary
*Attorney, Agent, or Firm*—Sughrue, Mion, Zinn, Macpeak & Seas

[57] ABSTRACT

A process of preparing galacto-oligosaccharides comprising the step of heating up lactose, or, a mixture of lactose and galactose under presence of an inorganic acid as a catalyst in an anhydrous powder condition.

4 Claims, 3 Drawing Sheets

METHOD FOR PREPARING GALACTO-OLIGOSACCHARIDES

BACKGROUND OF THE INVENTION

1. Field of the Invention

The present invention relates to a method for preparating galacto-oligosaccharides in which lactose, or both lactose and galactose are employed as their material(s).

In general, an oligosaccharide that contains galactose in its molecule is called a galacto-oligosaccharide.

2. Description of Prior Art

In the art of preparation of galacto-oligosaccharides, the following methods have been heretofore employed: the one to produce transglycosylated galacto-oligosaccharides to allow an enzyme generated from microorganism to act on lactose (Japanese Patent Publication (Examined) No. 58-20266 and Japanese Patent Publication (Examined) No. 60-25189); the one to use bean oligosaccharides from soybean milk whey (Japanese Patent Publication (Unexamined) No. 62-155082); the one for extraction to use raffinose of beet sugar (Japanese Patent Publication (Unexamined) No. 62-126951); and so on.

A problem exists in the results obtained through the mentioned known methods, however, that they are so low in purity of aimed galacto-oligosaccharides as to be more or less 50%, futher lower in sugar content of them, and not easy to treat because of their liquid state (about 75% in concentration). Therefore, it has been necessary for these conventional methods to additionally conduct a process of extracting galacto-oligosaccharides of higher purity and to purify them by some chromatographic method or the like. The compositions of the conventional galacto-oligosaccharides made known to the public are as shown in the following Table 1.

TABLE 1

|  | (1) | (2) | (3) |
|---|---|---|---|
| Tradename | Cup-oligo | Lacto-oligo-saccharides | Soybean-oligo-saccharides |
| Galacto-oligo-saccharide | 48 to 58 | 36.2 | 31.5 |
| Disaccharide | 7 to 10 | 26.1 | 44.7 |
| Monosaccharide | 30 to 40 | 37.7 |  |
| Other sugars |  |  | 23.7 |

Note:
(1) obtained from lactose produced by Nisshin Sugar Refinary;
(2) obtained from lactose produced by Yakult; and
(3) obtained from soybean produced by Calpis.

SUMMARY OF THE INVENTION

The present invention was made to solve the above-discussed problems pertinent to the prior arts.

It is, therefore, an object of the present invention to provide galacto-oligosaccharides of high purity, preferably in powder condition, through a simple method.

The inventors of the present application have been engaged in studying several methods to produce a product of highly pure galacto-oligosaccharides by more simple and easier method, and as a result, have successfully found a new method, quite different from the conventional ones, to obtain powdered galacto-oligosaccharides of high purity. In other words, the inventors have discovered that their object can be obtained by heating up lactose, or lactose and galactose with a small amount of acid as a catalyst in an anhydrous condition, thus accomplishing the invention.

Described now are materials to be preferably employed in the invention.

First, as for lactose to be used as a material, there is no restriction in its kind, thus all kinds of conventionally known lactose being widely employed. For example, lactose commercially available on the market can be employed, and each of $\alpha$-lactose, $\beta$-lactose and equilibrated lactose can be used in case of adding acid in a solution of lactose. In case of adding acid into powder of lactose, $\alpha$-lactose is recommendable.

Now $\alpha$-lactose, $\beta$-lactose, and equilibrated lactose are respectively defined as follows:

(1) $\alpha$-lactose:

This is the most common kind of lactose obtained by separating crystals out of a solution containing lactose crystallized at a relatively low temperature (usually below 94° C.).

(2) $\beta$-lactose:

This is a kind of lactose obtained by separating crystals out of a solution containing lactose crystallized at a high temperature (usually above 94° C.).

(3) Equilibrated lactose:

This is a kind of lactose obtained by spray-drying a solution containing lactose and is an amorphous powder containing $\alpha$-lactose and $\beta$-lactose in an approximate ratio of 4:6.

When dissolved in water, each of the mentioned lactoses presents the same containing ratio of $\alpha$-lactose and $\beta$-lactose just as that in equilibrated lactose with the lapse of time.

Secondly, galactose of an article commercially available on the market can be employed.

Mixture ratio of lactose and galactose to be used together should be 9:1 to 5:5, preferably 8:2 to 7:3 (by weight).

Thirdly, the acid catalysts to be utilized include hydrochloric acid, nitric acid, phosphoric acid, and sulfuric acid. However, those except hydrochloric acid are not preferable because of their restrictions in yield, possible corrosion of heating apparatus, and particularly food hygiene. A small amount of acid should be sufficient, and the amount of acid should preferably be in the range of 0.1% to 0.01% by weight to the total weight of lactose or both lactose and galactose (under dry condition).

Since acid will be well mixed with the material(s) being lactose alone or both lactose and galactose, the acid should be diluted to about 1% and sprayed into the material(s) with stirring toward dehydration, otherwise a fixed amount thereof should be added into a solution of the material(s) and the mixture should be powdered in spray-drying method or the like. Then, maintaining the mixture dehydrated at a temperature range from 100° C. to 200° C. for 0.5 to 3 hours, preferably 1 to 2 hours, will induce polymerization of the mixture to convert them into galacto-oligosaccharides. In this case, temperature lower than 100° C. will make it difficult to produce the aimed galacto-oligosaccharides, while temperature higher than 200° C., being too close to the melting point of lactose, will bring about fusion or coloration of the mixture. Therefore, the temperature should be kept within the mentioned range. Similarly, heating time less than one hour will cause particularly low yield, while heating time longer than 3 hours will cause coloration or scorching. Consequently, the time required for heating should be kept within the mentioned range.

Galacto-oligosaccharides obtained in the foregoing process are to be dissolved in water and neutralized, then decolorized, desalted, concentrated according to normal process, finally spray-dried to obtain a powdered product.

DESCRIPTION OF THE PREFERRED EMBODIMENTS

The present invention is now described in more details with reference to the following examples wherein, unless otherwise specified, all percentages and ratios therein are indicated by weight.

In this respect, acknowledgment (verification) that the ingredients were no doubt galacto-oligosaccharides, distribution of their molecular weight, and the composition of saccharides were conducted and measured with a solution which was hydrolyzed with acid and examined by means of a high performance liquid chromatography.

EXAMPLE 1:

5 ml of 1.0% solution of hydrochloric acid was added to 100 gs of α-lactose of an article commercially available on the market by spraying with compressed air and mixed evenly by means of a mixer, placed on an aluminum vat, pre-dried at a temperature of 80° C. for an hour in a drier, then converted by heating at a temperature of 180° C. for 3 hours.

The composition of saccharides obtained through the mentioned processes were as follows (hereinafter % by weight):

| Monosaccharide | 3.2% |
| Disaccharide (lactose) | 24.0% |
| Galacto-oligosaccharide | 72.8% |
| Average molecular weight | 950 |

Figure 1:
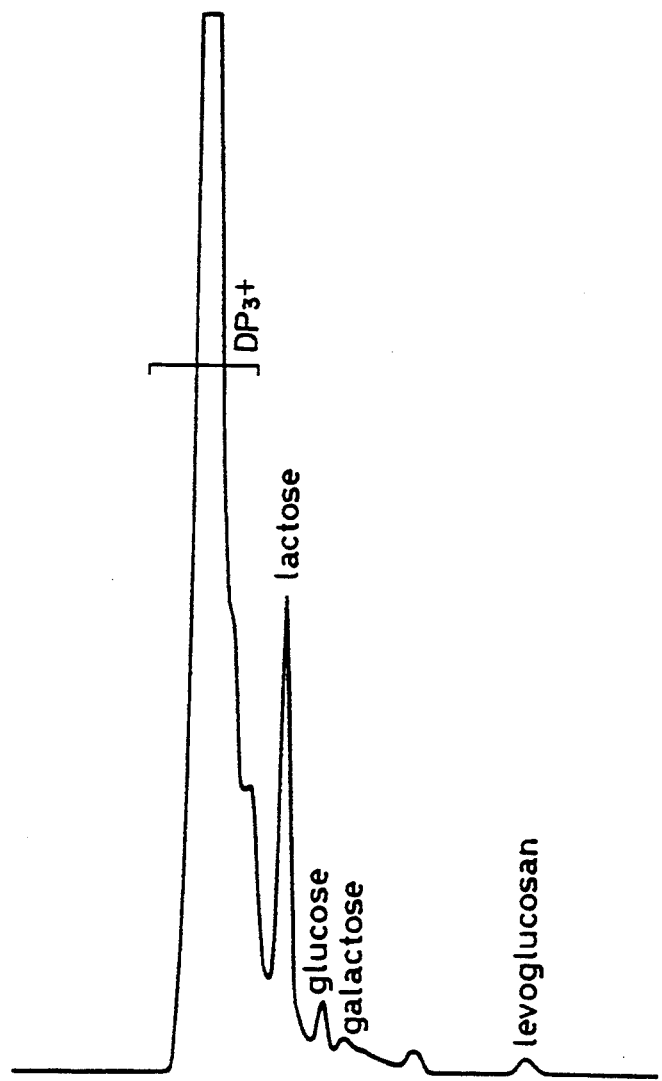
FIG. 1 shows a high performance liquid chromatogram illustrating the composition of saccharides obtained in Example 1 in accordance with the present invention.
Figure 2:
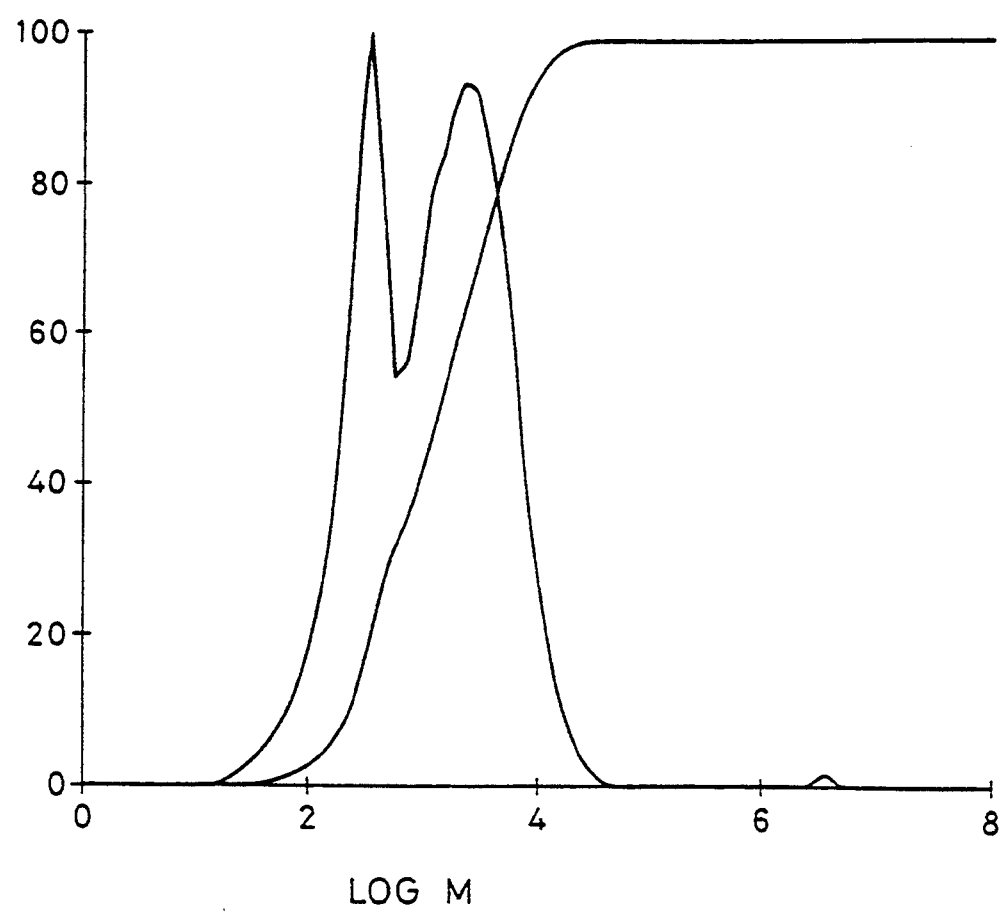
FIG. 2 shows a high performance liquid chromatogram to be used for measuring average molecular weight.
Figure 3:
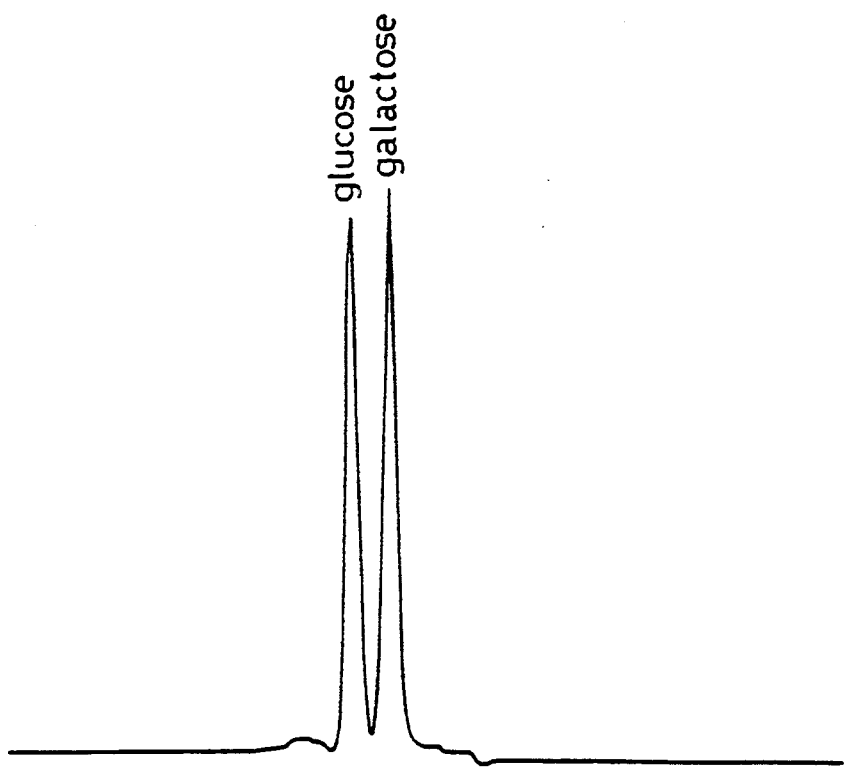
FIG. 3 shows a high performance liquid chromatogram indicating the results of the powder obtained and hydrolyzed with acid in order to verify that the saccharides obtained in Example 1 are surely galacto-oligosaccharides.

FIG. 1 shows a high performance liquid chromatogram indicating the above composition of saccharides. FIG. 2 shows a high performance liquid chromatograph to be used for measuring average molecular weight, and FIG. 3 shows a high performance liquid chromatogram of the hydrolyzates for verification of galacto-oligosaccharides.

EXAMPLE 2:

2000 Kgs of α-lactose commercially available on the market was dissolved in water to be a 40% solution, then 500 ppm of hydrochloric acid was added, and powdered with a spray-drier (with an inlet air temperature of 170° C., and outlet air temperature of 90° C. and an atomizer speed at 4500 r.p.m.). Then, 1900 Kgs of the powder obtained was put into a Rotary-Kiln-Type converter continuously to be heated at a temperature of 120° C. for one hour and a half.

The powder obtained through the above processes was dissolved in water and neutralized with sodium hydroxide, decolorized with activated charcoal, then desalted with ion-exchange resins and finally spray-dried to obtain 1800 Kgs of powder. The composition of saccharides of this powder were as follows:

| Monosaccharide | 4.0% |
| Disaccharide (lactose) | 8.0% |
| Galacto-oligosaccharide | 88.0% |
| Average molecular weight | 880 |

EXAMPLE 3:

120 gs of galactose and 500 ppm of hydrochloric acid were added to 1000 Kgs of equilibrated lactose commercially available on the market, and powdered with a spray-drier (with an inlet air temperature of 160° C., and outlet air temperature of 90° C., and an atomizer speed at 14400 r.p.m.). Then, 1000 gs of the powder obtained was put into an oil bath to be heated at a temperature of 120° C. for one hour and a half under mixing.

The powder obtained through the above processes was dissolved in water and neutralized with sodium hydroxide, decolorized with activated charcoal, then desalted with ion-exchange resins and finally spray-dried to obtain 900 Kgs of powder. The composition of saccharides of this powder were as follows:

| Monosaccharide | 3.9% |
| Disaccharide (lactose) | 11.1% |
| Galacto-oligosaccharide | 85.0% |
| Average molecular weight | 800 |

EXAMPLE 4:

500 gs of equilibrated lactose commercially available on the market was mixed with 500 gs of galactose, to which 50 ml of 1% solution of hydrochloric acid was added by spraying with compressed air, and pre-dried at a temperature of 80° C. for an hour in a converter in the same manner as Example 1, then heated at a temperature of 180° C. for 2 hours and a half.

The powder obtained through the above processes was dissolved in water and neutralized with sodium hydroxide, decolorized with activated charcoal, then desalted with ion-exchange resins and finally spray-dried to obtain 800 Kgs of powder. The composition of saccharides of this powder were as follows:

| Monosaccharide | 3.8% |
| Disaccharide (lactose) | 8.5% |
| Galacto-oligosaccharide | 87.7% |
| Average molecular weight | 785 |

EXAMPLE 5:

800 gs of equilibrated lactose commercially available on the market was mixed with 200 gs of galactose, to which 50 ml of 1% solution of hydrochloric acid was added by spraying with compressed air, and pre-dried at a temperature of 80° C. for an hour in a converter in the same manner as Example 1, then heated at a temperature of 160° C. for one hour and a half.

The powder obtained through the above processes was dissolved in water and neutralized with sodium hydroxide, decolorized with activated charcoal, then desalted with ion-exchange resins and finally spray-dried to obtain 820 Kgs of powder. The composition of saccharides of this powder were as follows:

|  |  |
| --- | --- |
| Monosaccharide | 5.2% |
| Disaccharide (lactose) | 10.4% |
| Galacto-oligosaccharide | 84.4% |
| Average molecular weight | 825 |

The present invention may be embodied in other specific forms without departing from the spirit or essential characteristics thereof. The foregoing embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A process for preparing a galacto-oligosaccharide, which consists essentially of heating dry powdery lactose at a temperature of 100°–200° C. for 0.5 to 3 hours in the presence of a catalytic amount of an inorganic acid selected from the group consisting of hydrochloric acid, nitric acid, phosphoric acid and sulfuric acid.

2. A process according to claim 1, wherein the lactose is at least one member selected from the group consisting of $\alpha$-lactose, $\beta$-lactose and equilibrated lactose.

3. A process according to claim 1, wherein the lactose is mixed with galactose.

4. A process according to claim 1, wherein the inorganic acid is hydrochloric acid.

* * * * *